United States Patent
Tseng et al.

(10) Patent No.: US 11,866,247 B2
(45) Date of Patent: Jan. 9, 2024

(54) GLOVE PACK AND A METHOD OF MAKING A GLOVE PACK

(71) Applicant: Inteplast Group Corporation, Livingston, NJ (US)

(72) Inventors: Pai-Mei Tseng, Somerset, NJ (US); Chih Jen Hsu, Closter, NJ (US); Jyh-Yao Raphael Li, Parsippany, NJ (US); Kelvin Yang, Madison, NJ (US)

(73) Assignee: INTEPLAST GROUP CORPORATION, Livingston, NJ (US)

( * ) Notice: Subject to any disclaimer, the term of this patent is extended or adjusted under 35 U.S.C. 154(b) by 0 days.

(21) Appl. No.: 17/406,854

(22) Filed: Aug. 19, 2021

(65) Prior Publication Data

US 2023/0059553 A1 Feb. 23, 2023

(51) Int. Cl.
*B65D 83/08* (2006.01)
*A61B 42/40* (2016.01)

(52) U.S. Cl.
CPC .......... *B65D 83/0835* (2013.01); *A61B 42/40* (2016.02)

(58) Field of Classification Search
CPC ................................................. B65D 83/0835
See application file for complete search history.

(56) References Cited

U.S. PATENT DOCUMENTS

| 5,087,234 A | 2/1992 | Prader et al. |
| 5,183,158 A | 2/1993 | Boyd et al. |
| 5,464,098 A | 11/1995 | Tseng et al. |
| 5,562,580 A | 10/1996 | Beasley et al. |
| 8,132,692 B2 | 3/2012 | Jordan |
| 9,084,445 B2 | 7/2015 | Lin et al. |
| 2006/0049199 A1* | 3/2006 | West ...................... A61B 42/40 221/26 |
| 2013/0104286 A1* | 5/2013 | Shawver ............. B29C 66/8242 2/168 |
| 2014/0026290 A1* | 1/2014 | Howland ............. A41D 19/015 66/174 |
| 2016/0152403 A1* | 6/2016 | Ray .................... B65D 83/0811 221/33 |
| 2020/0170320 A1* | 6/2020 | Robert ............... A41D 19/0082 |

FOREIGN PATENT DOCUMENTS

GB 2 451 450 A * 2/2009

* cited by examiner

*Primary Examiner* — Gene O Crawford
*Assistant Examiner* — Ayodeji T Ojofeitimi
(74) *Attorney, Agent, or Firm* — Stinson LLP

(57) ABSTRACT

Systems and methods of making a glove pack and for removing gloves from the glove pack are disclosed. The glove pack includes a stack of gloves. The stack of gloves includes a first glove engaging a second glove. The first and second gloves each have an exterior gripping surface. Each exterior gripping surface of the first and second gloves engages and adheres to the exterior gripping surface of the other of the first or second glove in the stack of gloves thereby adhering the first and second gloves together in the stack of gloves such that when the first glove is removed from the stack of gloves at least a portion of the second glove moves with the first glove.

17 Claims, 7 Drawing Sheets

GLOVE PACK AND A METHOD OF MAKING A GLOVE PACK

FIELD

The present disclosure generally relates to disposable gloves and, in particular, packs of disposable gloves.

BACKGROUND

Disposable plastic gloves are used to protect hands and fingers from items or contaminants commonly found in medical and hospital settings, food preparation areas, laboratories, manufacturing, households, and so on. Gloves are used to protects a user's hands and fingers from coming into contact and possibly contaminating or being contaminated by an item, such as a chemical, being handled by the user. Gloves often come in packs containing a plurality (e.g., 24, 50, 100, etc.) of gloves.

SUMMARY

In one aspect, a glove pack comprises a stack of gloves including a first glove engaging a second glove. The first and second gloves each have an exterior gripping surface. Each exterior gripping surface of the first and second gloves engages and adheres to the exterior gripping surface of the other of the first or second glove in the stack of gloves thereby adhering the first and second gloves together in the stack of gloves such that when the first glove is removed from the stack of gloves at least a portion of the second glove moves with the first glove.

In another aspect, a method of providing a plurality of gloves includes forming the plurality of gloves. Each glove has an exterior gripping surface. The method includes arranging the plurality of gloves in a stack of gloves such that the exterior gripping surfaces of adjacent gloves of the plurality of gloves engage and adhere to each other thereby adhering said adjacent gloves of the plurality of gloves together. The method also includes placing the stack of gloves in a glove package.

Other objects and features of the present disclosure will be in part apparent and in part pointed out herein.

BRIEF DESCRIPTION OF THE DRAWINGS

Corresponding reference numbers indicate corresponding parts throughout the drawings.

DETAILED DESCRIPTION

Figure 1:
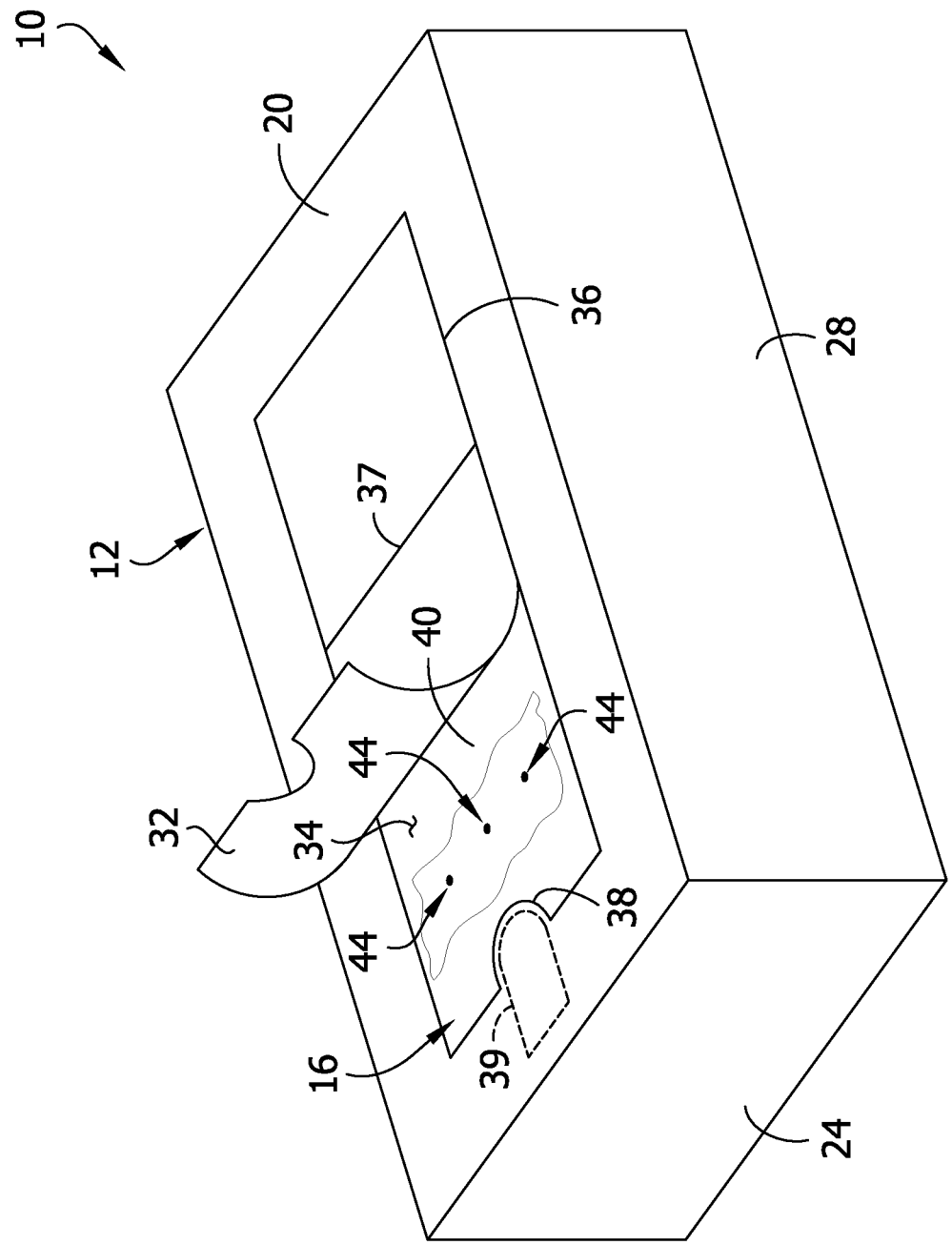
FIG. 1 is a perspective of a glove pack according to one embodiment of the present disclosure, with an opening section partially removed from a glove package of the glove pack.
Figure 3:
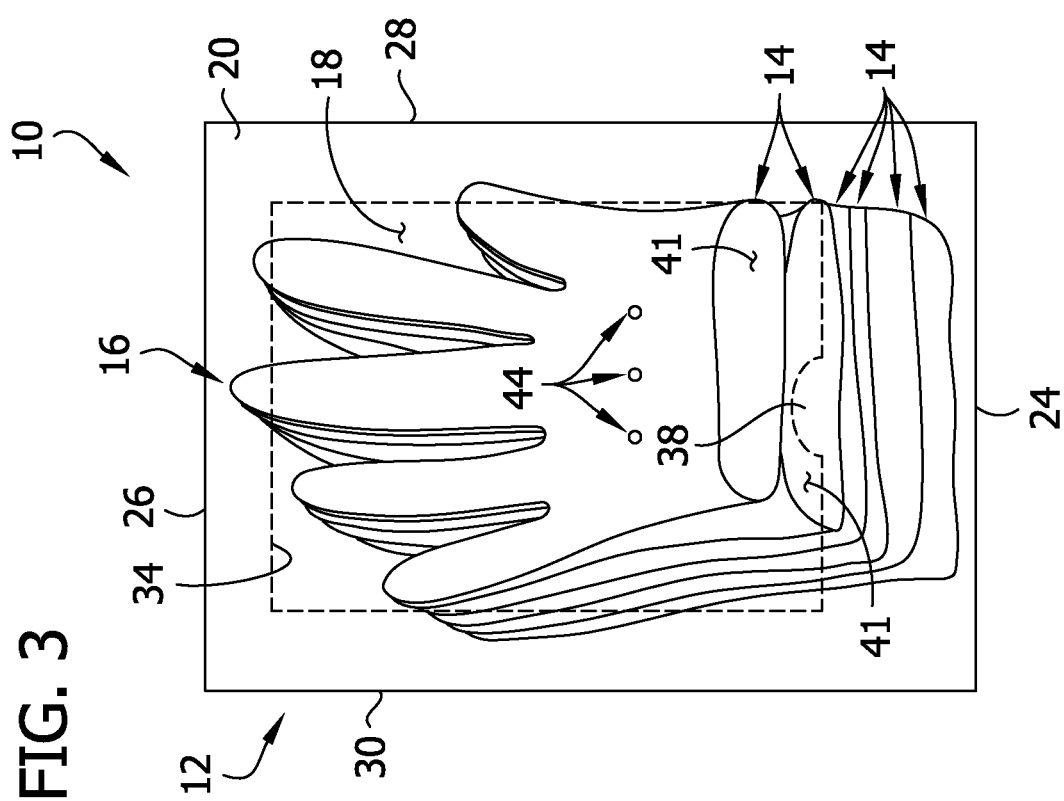
FIG. 3 is a schematic illustration similar to FIG. 2, showing the top-most glove in the stack of gloves being removed from the glove pack.

Referring to FIGS. 1-6, a glove pack according to one embodiment of the present disclosure is generally indicated at reference numeral 10. The glove pack 10 includes a glove package 12 containing a plurality of gloves 14 (e.g., a first glove, a second glove, a third glove, . . . , etc.) arranged in a stack 16. The gloves 14 and glove stack 16 are configured and arranged such that when the top-most glove of the glove stack is removed from the glove pack 10, the next subsequent top-most glove (which directly underlies the top-most glove) at least partially moves with the top-most glove to make it easier to also eventually remove and don this next subsequent top-most glove from the glove pack.

The glove package 12 defines an interior 18. The glove stack 16 is disposed within the interior 18 of the glove package 12. The glove package 12 includes opposite top and bottom walls 20, 22, opposite first and second end walls 24, 26, and opposite first and second side walls 28, 30. The walls 20, 22, 24, 26, 28, 30 bound the interior 18. In the illustrated embodiment, the glove package 12 has a generally rectangular cuboid shape, although other shapes are within the scope of the present disclosure. The interior 18 of the glove package is sized and shaped to receive one glove stack 16. In other embodiments, the interior of the glove package can be sized and shaped to receive and hold multiple (e.g., two, three, etc.) glove stacks. The glove package 12 may be made of paper board or any other suitable material.

The glove package 12 includes an opening section or panel 32. The opening panel is frangibly connected to the remainder of the package 12 and can be removed or partially removed from the glove package to create an opening 34 to access the gloves 14 in the interior 18 of the glove package. In the illustrated embodiment, the opening panel 32 is formed out of the top wall 20. A generally rectangular patterns of perforations 36 formed in the top wall 20 defines the opening panel 32. The pattern of perforations 36 allows the opening panel 32 to be manually removed from the top wall 20 by breaking and otherwise tearing the opening panel from the remainder of the top wall to create the opening 34. In the illustrated embodiment, the pattern of perforations 36 extends along all sides of the opening panel 32, such that the opening panel can be completely removed from the top wall 20. In another embodiment, the pattern of perforations 36 may extend along only some (e.g., three) sides of the opening panel 32 such that some of the sides of the opening panel can be torn from the top wall 20 to create the opening 34 but the opening panel remains attached to the top wall. The glove package 12 may also include another line of perforation 37 extending laterally across the opening panel 32 to allow for partial opening of the glove package by removing only a portion of the opening panel or only breaking the lines of perforation 36 to the additional line of perforation 37.

The glove package 12 is configured to restrict the movement of the remaining gloves 14 in the glove stack 16 when the top-most glove is removed from the glove package. Specifically, the glove package 12 restricts the movement of the next subsequent top-most glove 14 (e.g., a second glove or an underlying glove) when the top-most glove (e.g., a first glove or an overlying glove) is removed from the glove package. The glove package 12 includes a retainer or tab 38 configured to engage each glove 14. The tab 38 extends into the opening 34 such that when a glove moves in through the opening, the glove contacts the tab. In the illustrated embodiment, the tab 38 is integral with the top wall 20, is defined by the pattern of perforations 36 and is generally revealed when the opening panel 32 is at least partially separated from the top wall 20. In general, the tab 38 is positioned to engage the next subsequent top-most glove 14 to restrict the movement of this next subsequent top-most glove when the top-most glove is removed from the glove package 12. Further details on how the tab 38 restricts movement are described below. In addition, the top wall 20 may also restrict the movement of the gloves 14. Preferably, the opening 34 is smaller than the size of the gloves 14 such that the gloves will contact the portions (e.g., edges) of the top wall 20 defining the opening as each glove moves through the opening, thereby restricting movement. For example, in one embodiment, each glove 14 has a length of about 10 inches (about 25.4 cm) and a width of about 5 inches (about 12.7 cm) and the opening 34 has a length of about 6¾ inches (about 17.1 cm) and a width of 2¾ inches (about 7 cm).

Figure 8:
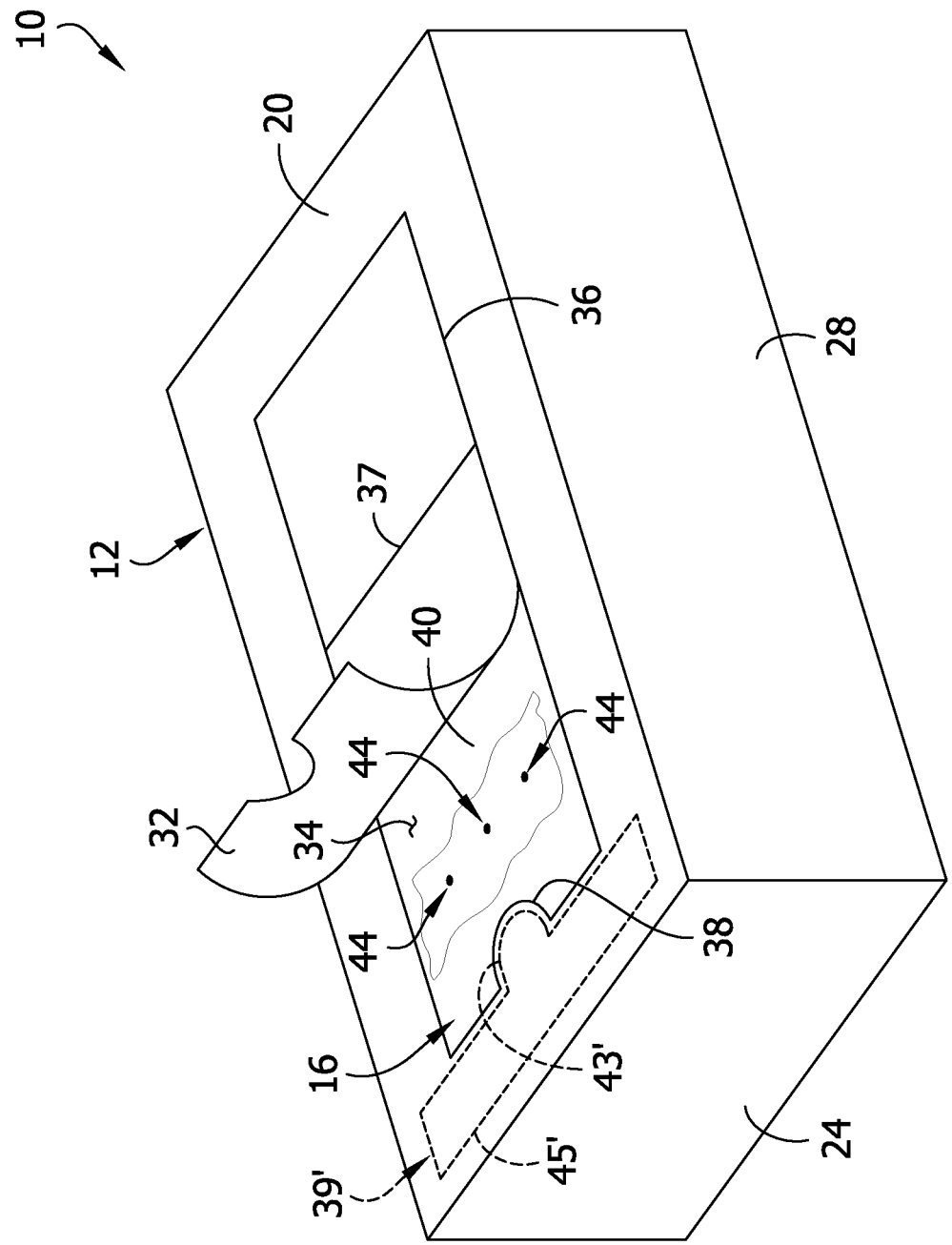
FIG. 8 is a perspective of the glove pack similar to FIG. 1, with another embodiment of a brace according to the present disclosure of the glove pack.

The glove package 12 may include a tab reinforcement or brace 39 (FIG. 1) to strengthen and stiffen the tab 38. The brace 39 can underlie or overlie the tab 38 and another portion of the top wall 20. The brace 39 prevents the tab 38 (which is made from the same material at the glove package, such as paper board) from crumpling, bending, or otherwise losing its rigidity as the gloves 14 are repeatedly removed from the glove stack 16. For reasons that will become apparent, the tab 38 may no longer be able to separate the gloves 14 as the gloves are removed from the glove stack if the tab loses its rigidity. The brace 39 may be made of plastic, metal, paper board, or the like. In the illustrated embodiment, the brace 39 generally reinforces only the tab 38. In other embodiments, the brace may also reinforce all or a part of the opening 34. One example of a brace, generally indicated at 39', that reinforces part of the opening 34 and the tab 38 is shown in FIG. 8. In this embodiment, the brace 39' includes a tab reinforcement portion 43' that reinforces the tab 38 and an opening reinforcement portion 45' that reinforces the opening 34. Specifically, the opening reinforcement portion 45' reinforces the edge of the top wall 20 from which the tab 38 extends into the opening 34. In addition to the tab 38, this edge of the top wall 20 may also lose its rigidity as the gloves 14 are repeatedly removed from the glove stack 16.

As shown in FIGS. 2-6, the gloves 14 are arranged in the glove stack 16. The gloves 14 are arranged one on top of another such that each glove 14 can be individually removed or withdrawn, one after another, from the glove package 12 (via the opening 34). Each glove 14 engages another glove in the glove stack 16. Specifically, the top-most glove 14 (e.g., a first glove) engages or rests on the next subsequent (e.g., second) top-most glove and this second top-most glove engages or rests on the third top-most glove and so on. Each glove 14 in the glove stack 16 is generally the same. Each glove 14 may be considered a disposable glove and is preferably made of a polyolefin, such as polyethylene, polypropylene, etc., although other materials are within the scope of the present disclosure. The film used to form the gloves 14 can be mono-extruded or co-extruded, and the film can be formed into the gloves in a suitable manner such as by a die cutting and sealing process, as generally known in the art.

Each glove 14 has an exterior gripping surface 40 on the exterior of the glove 14. Preferably, the exterior gripping surface 40 is the entire exterior surface of the glove 14. The exterior gripping surface 40 of each glove 14 engages and adheres (e.g., sticks to, clings) to the exterior griping surface of the glove immediately below itself in the glove stack 16 thereby adhering these two gloves together. In other words, for each set of two adjacent gloves 14 in the glove stack 16, the exterior gripping surface 40 of an upper or first glove engages and adheres to the exterior griping surface of the immediately lower or second glove thereby adhering these adjacent gloves together in the glove stack. As a result of this adhesion, when the upper or first glove 14 (e.g., top-most glove) is removed from the glove stack 16, at least a portion of the immediately lower or second glove (e.g., next subsequent top-most glove) moves with the upper glove. Each glove 14 includes a mouth 41 through which a user may insert a hand in order to put on the glove. Preferably, the adhesion of the exterior gripping surfaces 40 of the adjacent (e.g., first and second) gloves 14 is at least adjacent the mouths 41 of the respective gloves so that when the upper or first glove is removed from the glove stack 16, the mouth of the lower or second glove is at least partially opened. The tab 38 of the glove package 12 is arranged to extend into the mouth 41 of the lower or second glove 14 when the upper or first glove is removed from the glove package to hold the mouth of the lower or second glove at least partially open once the upper or first glove is removed from the glove stack 16. Specifically, by entering the mouth 41 of the glove 14, the tab 38 separates the top layer of the glove from the bottom layer of the glove. This makes it easier to put on the lower or second glove 14 once it is also removed from the glove stack 16 and also makes it easier to grab the lower or second glove to remove the lower or second glove from the glove package 12.

As used herein, the terms "adhere," "adheres," "adhesion," and the like do not require absolute fixation between the gloves 14 via the exterior gripping surfaces 40. Instead, these terms used to describe the slight or weak bonding that occurs between the gloves 14 via the exterior gripping surfaces 40. The bonding is weak in the sense that is can be easily overcome, such as by manually pulling the gloves 14 apart or such as by the tab 38 and/or the top wall 20 retaining the next subsequent top-most glove in the glove stack 16 as the top-most glove is manually removed from the glove stack 16. The separation of adjacent gloves 14 can be achieved without significant damage to either of the previously adhered surfaces. Thus, this weak bonding is temporary and does not join the gloves in a permanent manner. Instead, the weak bonding is sufficient enough so as to allow the gloves 14 to move together when the gloves are not otherwise retrained from moving. For example, the weak bonding is sufficient enough to overcome the force of gravity such that when the top-most glove 14 is removed or lifted off the glove stack 16, at least a portion of the next subsequent top-most glove moves with it. This movement occurs without a user having to grab the next subsequent top-most glove 14 at the same time as the top-most glove. The adhesion between the gloves 14 occurs without using other techniques for adhesion such as using adhesives or thermal bonding.

In one embodiment, the exterior gripping surface 40 of each glove 14 has a large coefficient of friction. Preferably, the exterior gripping surface 40 of each glove 14 has a coefficient of friction equal to or greater than about 0.3, as measured according to ASTM D1894. In this embodiment, due to the large coefficient of friction, the exterior gripping surfaces 40 of adjacent gloves 14 generally adhere to each other as described herein. In another embodiment, the exterior gripping surface 40 of each glove 14 has a high surface energy. Preferably, the exterior gripping surface 40 of each glove 14 has a surface energy equal to or greater than about 38 dyne/cm, or more preferably equal to or greater than about 42 dyne/cm, or more preferably equal to or greater than about 46 dyne/cm, as measured according to ASTM D2578. In this embodiment, due to the large surface energy, the exterior gripping surfaces 40 of adjacent gloves 14 generally adhere to each other as described herein. In one embodiment, the exterior gripping surface 40 of each glove 14 is a corona treated surface. The high surface energy of the exterior gripping surface 40 of each glove 14 is formed by a corona treatment on the exterior surface of each glove. Other ways of creating the high surface energy exterior gripping surface 40 are within the scope of the present disclosure. For example, the high surface energy can be created using a flame treatment, a chemical treatment, etc.

Each glove 14 may have a non-gripping interior surface 42. This makes it easier to put on and take off each glove 14. For example, in one embodiment, the non-gripping surface 42 of each glove has a low coefficient of friction. The coefficient of friction of the non-gripping interior surface 42 is lower than the coefficient of friction of the exterior gripping surface 40. Preferably, the ratio of the coefficient of friction of the exterior gripping surface 40 to the coefficient of friction of the interior gripping surface 42 is at least about 1.5. This facilitates the opening of the mouth 41 of the underlying glove 14 when the overlying glove is removed from the glove stack 16 while also keeping the adhesion between the overlying and underlying gloves in the glove stack to move the underlying glove, as described herein. The non-gripping interior surface 42 of each glove 14 has a coefficient of friction less than about 0.3, or preferably less than about 0.2, as measured by ASTM D1894. In another embodiment, the non-gripping interior surface 42 of each glove 14 has a low surface energy. Preferably, the non-gripping interior surface 42 of each glove 14 has a surface energy less than about 38 dyne/cm, or more preferably equal to or less than about 36 dyne/cm, or more preferably equal to or less than about 34 dyne/cm, as measured according to ASTM D2578. This facilitates the opening of the mouth 41 of the underlying glove 14 when the overlying glove is removed from the glove stack 16 while also keeping the adhesion between the overlying and underlying gloves in the glove stack to move the underlying glove, as described herein.

Figure 4:
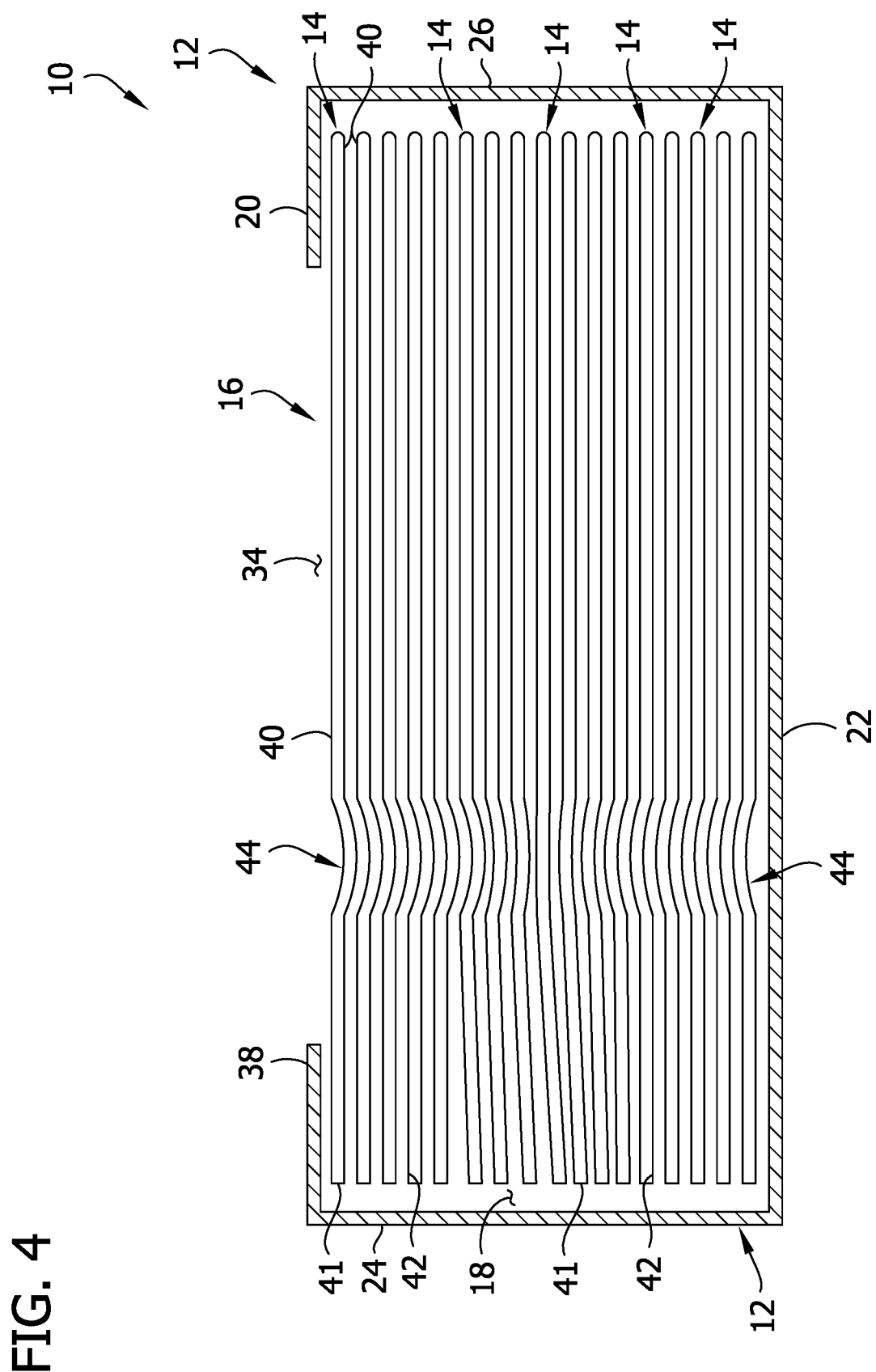
FIG. 4 is a schematic vertical section through the glove pack, before any gloves are removed from the glove package.
Figure 5:
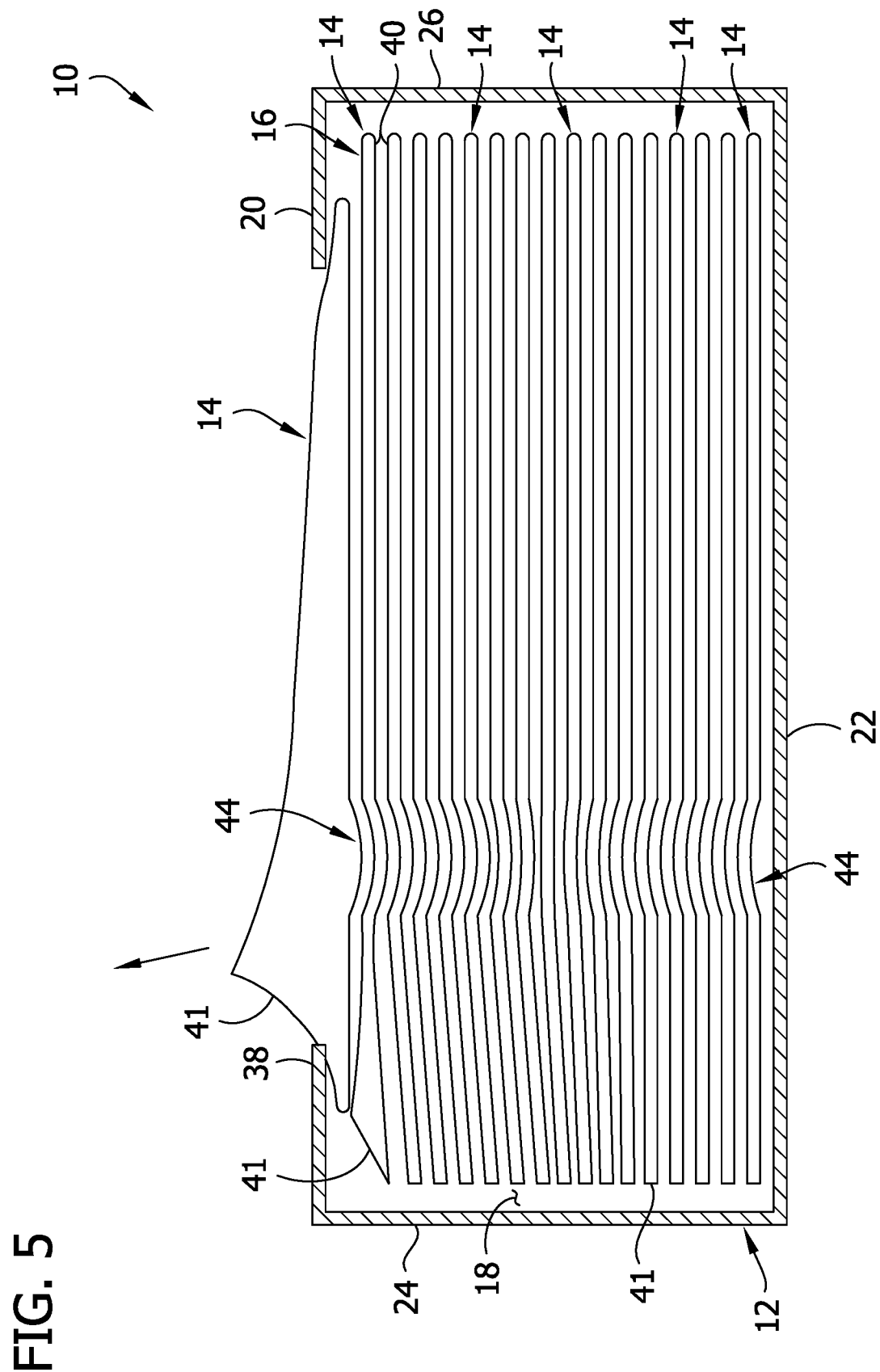
FIG. 5 is the schematic vertical section of FIG. 4, but showing the top-most glove in the stack of gloves being removed from the glove pack.
Figure 6:
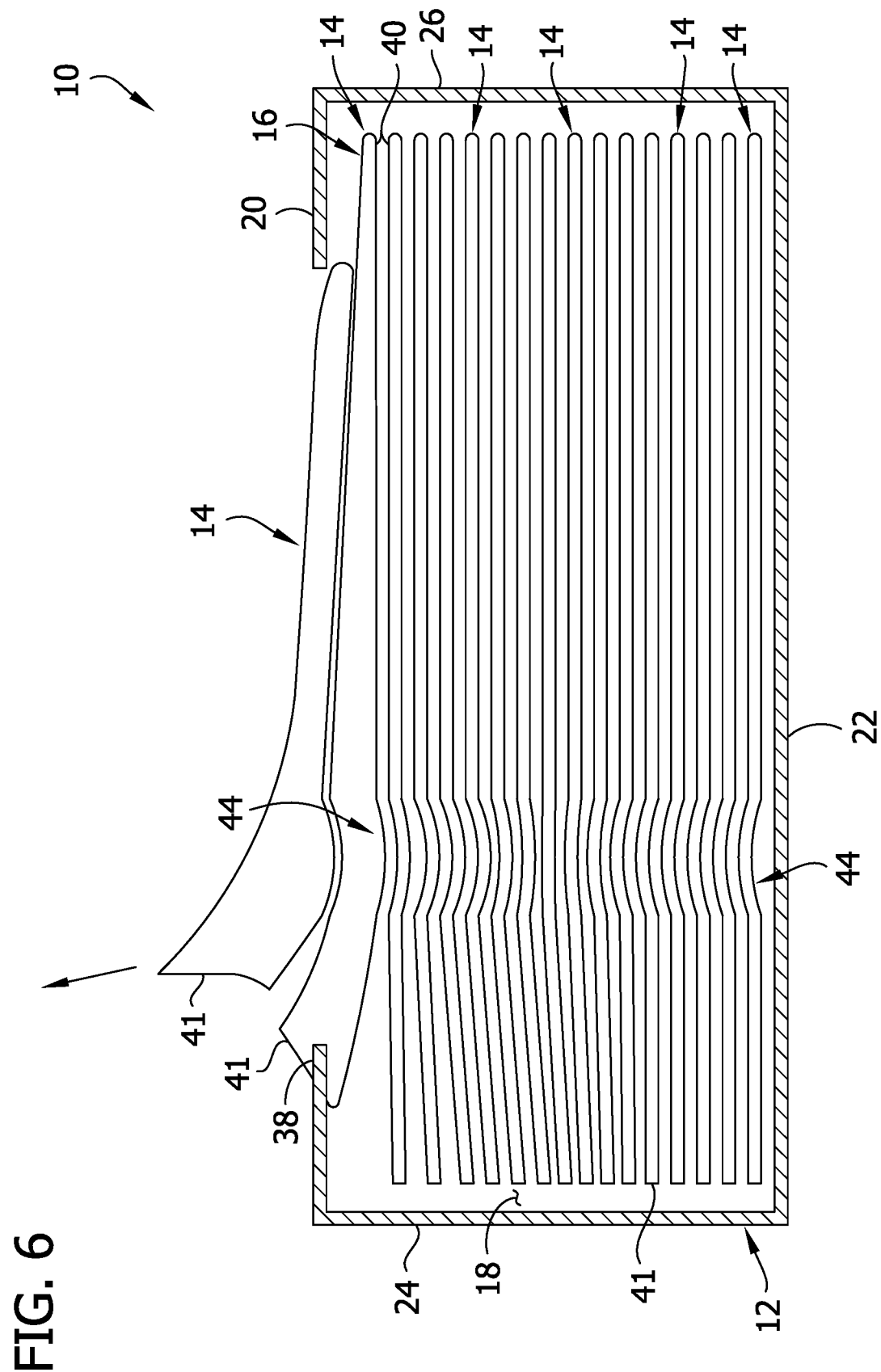
FIG. 6 is the schematic vertical section of FIG. 4, but showing the top-most glove in the stack of gloves nearly finished from being removed from the glove pack.

The glove stack 16 is preferably compressed. As a result, the gloves 14 (e.g., each set of adjacent gloves) are forced together. This compression of the gloves 14 in the glove stack 16 facilitates the formation of the adhesion between the adjacent gloves 14 via the gripping exterior surfaces 40. Each glove 14 may include one or more impressions or indentations 44. In the illustrated embodiment, each glove 14 includes three impressions 44 although more or fewer impressions are within the scope of the present disclosure. The impressions 44 of each glove 14 are formed by the compression. The glove stack 16 may be compressed in any suitable manner. For example, in the illustrated embodiment, the glove stack 16 is compressed from above and below. In other embodiments, the glove stack may be compressed only from above or only from below, such as by compressing the glove stack against a flat surface (from either above or below). As shown in FIGS. 4-6, the impressions 44 of each glove 14 engage the adjacent glove (e.g., the impression thereof) to facilitate the adhesion of the exterior gripping surfaces 40 of each set of adjacent gloves in the glove stack 16. Due to the non-gripping interior surface 42, the compression and resulting impressions do not result in the inner surfaces of each glove 14 being adhered together. This permits the mouth 41 of each glove 14 to be easily opened, such as by removing the top-most glove, to make it easy to put the glove on the hand of a user.

Figure 2:
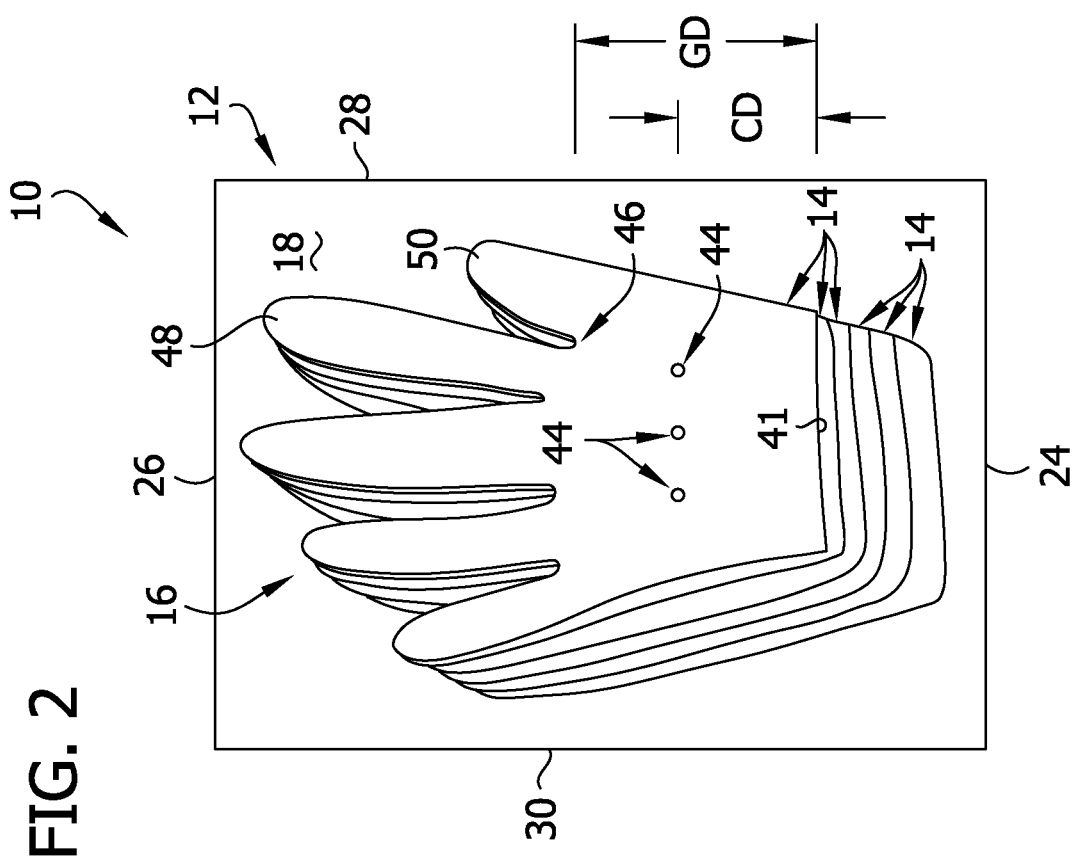
FIG. 2 is a schematic illustration of a stack of gloves in the glove package of the glove pack.

The glove stack 16 is compressed at a location on each glove 14 (e.g., the impressions 44 are disposed at the location). The location is spaced a compression distance CD (FIG. 2) from the mouth 41 of the glove 14. In the illustrated embodiment, the impressions 44 are all arranged along an imaginary axis that extends laterally or widthwise across the glove 14. The imaginary axis extents generally parallel to the mouth 41 of the glove 14 and is spaced the compression distance CD from the mouth of the glove. Thus, the impressions 44 are all located the same distance from the mouth 41 of the glove 14 (e.g., located at the same lateral location). The compression distance CD is a function of a thumb gap distance GD (FIG. 2). Preferably, the compression distance CD is within the inclusive range of about 0.1 times the thumb gap distance GD to about 0.9 times the thumb gap distance, and even more preferably is within the inclusive range of about 0.15 times the thumb gap distance GD to about 0.5 times the thumb gap distance. It is believed compressing the glove stack 16 within this range provides the best performance—i.e., moving a portion of the underlying glove 14 along with the upper glove being removed from the glove stack 16, and opening the mouth 41 of the underlying glove. When the gloves 14 are arranged in the glove stack 16, the gloves may not be perfectly aligned. If the compression location is too close to the mouth 41 of the gloves 14, the compression may miss some of the gloves 14 in the glove stack such that those gloves will not be imparted with impressions 44, preventing the adhesion of the exterior gripping surfaces 44. If the compression location is too close to the fingers of the glove 14, the mouth 41 of each glove 14 may not be opened when the overlying glove 14 is removed from the glove stack 16. The thumb gap distance GD is measured between a gap point 46 between the index finger portion 48 and the thumb finger portion 50 of the glove 14. The gap point 46 is the location on the perimeter of the glove 14 between the index finger portion 48 and the thumb finger portion 50 of the glove that is closest to the mouth 41 of the glove. The thumb gap distance GD is the shortest distance between the gap point 46 and the mouth 41 of the glove 14. In other words, the thumb gap distance GD is generally parallel to the length of the glove 14. The gloves 14 are generally vertically aligned when in the glove stack 16 such that the location of the compression (e.g., the location of the impressions 44) is generally the same on each glove. Other arrangements of the impressions are within the scope of the present disclosure. For example, the impression can be arranged along a curved (e.g., concave or convex relative to the mouth of the glove) line, in a V-shape arrangement or other arrangement may be used.

Figure 7:
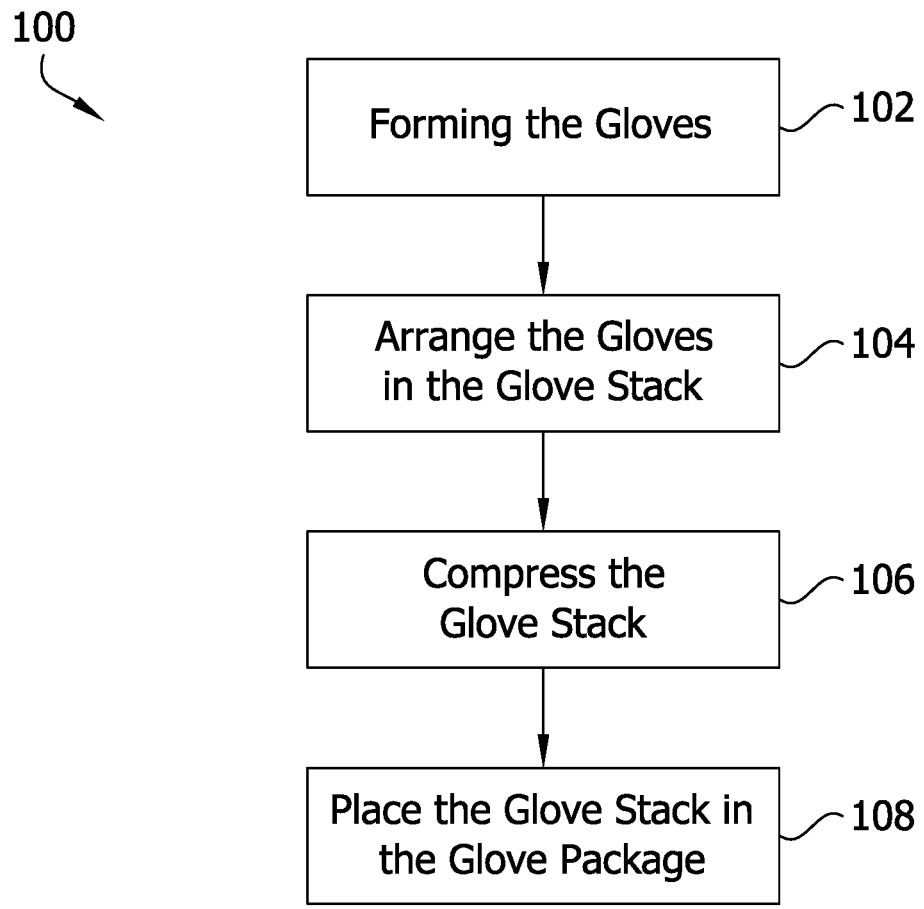
FIG. 7 is an example flow diagram of the manufacture of the glove pack according to one embodiment of the present disclosure.

Referring to FIG. 7, a method of manufacturing the glove pack 10 (broadly, handling the plurality of gloves 14) is generally indicated at 100. Initially, at step 102, the gloves 14 are formed or created. As mentioned above, the gloves 14 can be formed using conventional die cut and sealing processes from a mono-extruded or co-extruded film tube. Forming the gloves 14 includes at least one of making the exterior gripping surface 40 of each glove out of a material having a large coefficient of friction, such as a low density polyethylene (or a polyethylene mixture comprising one or more of ethylene-vinyl acetate copolymer and metallocene), making the exterior gripping surface of each glove out of material having a high surface energy, or treating the exterior gripping surface of each glove to have a high surface energy such as with a corona treatment. For example, in the embodiment employing a large coefficient of friction, the gloves 14 are formed from multi-layer co-extruded film, where the outer layer (forming the exterior gripping surface 40) has the large coefficient of friction and the inner layer (forming the non-gripping interior surface 42) has a lower coefficient of friction. In another example, in the embodiment employing the high surface energy, the material forming the glove 14 is less important because the material can be treated, as described herein, in order to give the material a high surface energy. Accordingly, in this embodiment, the gloves 14 can be mono-extruded or co-extruded.

After the gloves 14 are formed, the gloves 14 are arranged in the glove stack 16 at step 104. By arranging the gloves 14 in the glove stack 16, the exterior gripping surfaces 40 of adjacent gloves in the glove stack engage and adhere to each other, thereby adhering the adjacent gloves together, as described herein. After the gloves 14 are stacked, the gloves (e.g., the glove stack 16) are compressed together at step 106. The glove stack 16 can be compressed together at generally room temperature (about 72 degrees F.) or at a raised temperature (about 212 degrees F.), that is below the melting temperature of the material forming each glove 14. It is believed compressing the gloves 14 together at the raised temperature results in better adhesion between the adjacent gloves. Any suitable member can be used to compress the glove stack 16, such as bar, cylinder, pin, etc.), with corresponding features to the make the impressions 44. At step 108, the glove stack 16 is placed in the glove package 12. In one embodiment, the glove package 12 (specifically the interior 18 thereof) is smaller than the gloves 14. Specifically, a length and/or width of the interior 18 can be smaller than the corresponding length and/or width of the gloves 14. For example, when each glove 14 has a length of about 10 inches (about 25.4 cm) and a width of about 5 inches (about 12.7 cm), the interior 14 of the glove package 12 may have a length of about 9¼ inches (about 23.5 cm) and a width of about 5 inches (about 12.7 cm). The same size of glove package 12 can be used to package different sizes (e.g., small, medium, large, extra large, etc.) of gloves.

Referring back to FIGS. 4-6, to remove a glove 14 from the glove package 12, first the opening 34 is formed by separating (partially or fully) the opening panel 32 from the remainder of the top wall 20. FIG. 4 shows the opening panel 32 fully removed from the top wall 20. Preferably, the opening 34 is aligned with and exposes the location of the compression (e.g., the impressions 44) of the gloves 14 in the glove stack 16. This arrangement ensures the adhesion between the gloves 14 will result in the top-most glove moving the next subsequent top-most glove when the top most glove is moved through the opening 34. After the opening 34 is formed, the user grabs the top-most glove 14 and begins removing it from the glove package 12 and the glove stack 16 by pulling the top-most glove through the opening 34, as shown in FIG. 5. As the user moves (e.g., removes) the top-most glove 14, at least a portion of the next subsequent top-most glove moves with it. Specifically, at least the portion of the next subsequent top-most glove 14 defining the mouth 41 moves with the top-most glove. As the user continues to pull the top-most glove 14 out of the glove package 12, the adhesion between the top-most glove and the next subsequent top-most glove opens the mouth 41 of the next subsequent top-most glove (e.g., the underlying glove). In particular, the adhesion between the top-most glove 14 and the next subsequent top-most glove drags the upper layer of the next subsequent top-most glove through the opening 34, thereby opening the mouth 41 of the next subsequent top-most glove. Continued movement of the top-most glove 14 moves the mouth 41 of the next subsequent top-most glove such that the tab 38 extends into the mouth of the next subsequent top-most glove (e.g., moves the upper layer of the next subsequent top-most glove around the tab), as shown in FIG. 6. The tab 38 may then engage the interior surface 42 of the lower layer of the next subsequent top-most glove 14 to retain this glove in the glove package (FIG. 6). Contact between the next subsequent top-most glove 14 and the top wall 20 (e.g., edges defining the opening 34) may also facilitate the retention. By retaining the next subsequent top-most glove 14, a sufficient amount of force is applied (via the tab 38 and/or top wall 20) to break the adhesion between the top-most glove and the next subsequent top-most glove. As a result, the top-most glove 14 is released from the stack by the user and the next subsequent top-most glove is retained in the glove package 12. Moreover, by extending into the mouth 41 of the next subsequent top-most glove 14, the tab 38 holds the mouth of the next subsequent top-most glove at least partially open after the adhesion with the top-most glove is broken. In other words, after the top-most glove is removed from the glove stack 16, a portion (e.g., an upper layer) of the next subsequent top-most glove is disposed above the tab 38 and a portion (e.g., a lower layer) of the next subsequent top-most glove is disposed below the tab. In one embodiment, the material on the top surface of each glove 14 may be slightly shorter than the material of the bottom surface or otherwise formed to facilitate engagement of the tab 38 with the bottom surface of the next glove in the stack. Once the top-most glove 14 is removed, the next subsequent top-most glove becomes the top-most glove and the process repeats as each glove is drawn from the glove package 12.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above products and methods without departing from the scope of the disclosure, it is intended that all matter contained in the above description shall be interpreted as illustrative and not in a limiting sense.

What is claimed is:

1. A glove pack comprising:
a stack of gloves including a first glove engaging a second glove, the first and second gloves each having an exterior gripping surface, each exterior gripping surface of the first and second gloves engaging and adhering to the exterior gripping surface of the other of the first or second glove in the stack of gloves thereby adhering the first and second gloves together in the stack of gloves such that when the first glove is removed from the stack of gloves at least a portion of the second glove moves with the first glove;
wherein the first glove includes one or more impressions engaging the second glove to facilitate adhesion of the exterior gripping surfaces of the first and second gloves.

2. The glove pack of claim 1, wherein each exterior gripping surface of the first and second gloves has the large coefficient of friction, the large coefficient of friction of each exterior gripping surface of the first and second gloves being equal to or greater than about 0.3.

3. The glove pack of claim 1, wherein each exterior gripping surface of the first and second gloves has the high surface energy, the high surface energy of each exterior gripping surface of the first and second gloves being equal to or greater than about 38 dyne/cm.

4. The glove pack of claim 3, wherein each exterior gripping surface of the first and second gloves is a corona treated surface.

5. The glove pack of claim 1, wherein the adhesion of the exterior gripping surfaces of the first and second gloves is adjacent mouths of the respective first and second gloves such that when the first glove is removed from the stack of gloves the mouth of the second glove is at least partially opened.

6. The glove pack of claim 1, wherein the stack of gloves is compressed such that the first and second gloves are adhered together.

7. The glove pack of claim 6 wherein the stack of gloves is compressed at a location on the first glove from a mouth of the first glove that is within the inclusive range of about 0.15 times a thumb gap distance to about 0.5 times the thumb gap distance, wherein the thumb gap distance is measured between a gap point between an index finger portion and a thumb portion of the first glove and the mouth of the first glove, wherein the gap point is the location on a perimeter of the first glove between the index finger portion and the thumb portion of the first glove that is closest to the mouth of the first glove, and wherein the thumb gap distance is the shortest distance between the gap point and the mouth.

8. The glove pack of claim 1, further comprising a glove package defining an interior, the stack of gloves disposed within the interior of the glove package, the glove package configured to restrict the movement of the second glove when the first glove is removed from the glove package.

9. The glove pack of claim 8, wherein the glove package includes a tab positioned to engage the second glove to restrict the movement of the second glove when the first glove is removed from the glove package, the tab arranged to extend into a mouth of the second glove when the first glove is removed from the glove package to hold the mouth of the second glove at least partially open once the first glove is removed from the stack of gloves.

10. The glove pack of claim 1, wherein the first and second gloves each have an interior surface, the coefficient of friction being less than about 0.3 or the surface energy being less than about 38 dyne/cm for each interior surface of the first and second gloves.

11. The glove pack of claim 1, wherein the first and second gloves comprise polyolefin.

12. A method of providing a plurality of gloves, the method comprising:
forming the plurality of gloves, each glove having an exterior gripping surface, wherein forming the plurality of gloves includes at least one of making the exterior gripping surface of each glove out of a material having a large coefficient of friction or treating the exterior gripping surface of each glove to have a high surface energy;
arranging the plurality of gloves in a stack of gloves such that the exterior gripping surfaces of adjacent gloves of the plurality of gloves engage and adhere to each other thereby adhering said adjacent gloves of the plurality of gloves together, further comprising compressing the plurality of gloves together in the stack to form one or more impressions in a first glove of an adjacent pair of gloves in the stack, the impressions engaging a second glove of the adjacent pair of gloves in the stack to adhere the exterior gripping surfaces of the first and second gloves together;
placing the stack of gloves in a glove package.

13. The method of claim 12, further comprising, after said arranging the plurality of gloves in the stack of gloves, compressing the plurality of gloves in the stack of gloves together.

14. The method of claim 13, wherein the plurality of gloves in the stack of gloves is compressed together at a location on each glove from a mouth of each glove that is within the inclusive range of about 0.15 times a thumb gap distance to about 0.5 times the thumb gap distance, wherein the thumb gap distance for each glove is measured between a gap point between an index finger portion and a thumb portion of said respective glove and the mouth of said respective glove, wherein the gap point for each glove is the location on a perimeter of said respective glove between the index finger portion and the thumb portion of said respective glove closest to the mouth of said respective glove, and wherein the thumb gap distance of each glove is the shortest distance between the gap point of said respective glove and the mouth of said respective glove.

15. The method of claim 12, wherein the plurality of gloves includes adjacent first and second gloves adhered to each other by the exterior griping surfaces of the first and second gloves so that when the first glove of the plurality of gloves is removed from the glove package and the stack of gloves, at least a portion of the second glove is removed with the first glove.

16. The method of claim 12, further comprising providing a retainer on the package to retain the second glove from being removed from the glove package when the first glove is being removed, the retainer extending into a mouth of the second glove to hold the mouth of the second glove at least partially open.

17. A glove pack comprising:
a stack of gloves including a first glove engaging a second glove, the first and second gloves each having an exterior gripping surface, each exterior gripping surface of the first and second gloves engaging and adhering to the exterior gripping surface of the other of the first or second glove in the stack of gloves thereby adhering the first and second gloves together in the stack of gloves such that when the first glove is removed from the stack of gloves at least a portion of the second glove moves with the first glove; and
a glove package defining an interior, the stack of gloves disposed within the interior of the glove package, the glove package configured to restrict the movement of the second glove when the first glove is removed from the glove package, the glove package including a tab positioned to engage the second glove to restrict the movement of the second glove when the first glove is removed from the glove package, the tab arranged to extend into a mouth of the second glove when the first glove is removed from the glove package to hold the mouth of the second glove at least partially open once the first glove is removed from the stack of gloves.

* * * * *